United States Patent [19]

Semler et al.

[11] 4,085,129

[45] Apr. 18, 1978

[54] PROCESS FOR THE PREPARATION OF CHLOROFORMIC ACID ARYL ESTERS AND CYCLIC CARBONATES

[75] Inventors: Günther Semler, Kelkheim, Taunus; Georg Schaeffer, Hofheim, Taunus, both of Germany

[73] Assignee: Hoechst Aktiengesellschaft, Frankfurt am Main, Germany

[21] Appl. No.: 727,332

[22] Filed: Sep. 28, 1976

Related U.S. Application Data

[63] Continuation-in-part of Ser. No. 543,340, Jan. 23, 1975, abandoned, which is a continuation of Ser. No. 265,557, Jun. 23, 1972, abandoned.

[30] Foreign Application Priority Data

Jun. 25, 1971 Germany .............................. 2131555
Mar. 20, 1972 Germany .............................. 2213408

[51] Int. Cl.$^2$ ............................................. C07C 68/02
[52] U.S. Cl. .................................................. 260/463
[58] Field of Search ......................................... 260/463

[56] References Cited

U.S. PATENT DOCUMENTS

| 3,170,946 | 2/1965 | Kilsheimer et al. | 260/463 |
| 3,211,774 | 10/1965 | Stephens | 260/463 |
| 3,211,776 | 10/1965 | Stephens | 260/463 |
| 3,255,230 | 6/1966 | Kurkjy et al. | 260/463 |

FOREIGN PATENT DOCUMENTS 2,007,804  1/1970  France ................................ 260/463

OTHER PUBLICATIONS

Kirk-Othmer, Encyclopedia of Chem. Technology, 2nd ed., vol. 4, Interscience Publishers, N.Y. (1964), p. 386.
Cotter et al., Chemistry & Industry, pp. 791-793, 5/8/65.

Primary Examiner—Joseph Paul Brust
Assistant Examiner—Robert C. Whittenbaugh
Attorney, Agent, or Firm—Curtis, Morris & Safford

[57] ABSTRACT

A process for the preparation of chloroformic acid aryl-esters and cyclic carbonates of aryl compounds containing at least two phenolic hydroxy groups wherein aromatic compounds containing one or more hydroxy groups linked to an aromatic nucleus, are reacted with phosgene in the presence of catalytic amounts of N,N-disubstituted acid amide either under pressure or without pressure while removing the hydrogen chloride continuously from the reaction mixture. This improved process results in almost quantitative or very high yields of pure products and avoids problems such as disposal of waste water.

11 Claims, No Drawings

PROCESS FOR THE PREPARATION OF CHLOROFORMIC ACID ARYL ESTERS AND CYCLIC CARBONATES

This application is a continuation-in-part of copending application Ser. No. 543,340 filed Jan. 23, 1975, now abandoned, which was a continuation of application Ser. No. 265,557, filed June 23, 1972, now abandoned. The present invention relates to a process for the preparation of chloroformic acid aryl esters and cyclic carbonates of aryl compounds containing at least two phenolic hydroxy groups.

The preparation is carried out by reacting aromatic compounds containing phenolic hydroxy groups with phosgene in the presence of catalytic amounts of a N,N-disubstituted acid amide.

The preparation of chloroformic acid esters from alcohols or phenols and phosgene is known. While the reaction with alcohols already occurs at low temperatures and in the absence of a catalyst, the reaction of phenols with phosgene cannot be effected without the addition of hydrogen-chloride-binding substances. For this purpose, tertiary amines, such as N, N-dimethylaniline (cf. Ullmann, Encyclopadie der technischen Chemie, vol. 5, pages 380 et seq., 1954) or also aqueous alkali (cf. German Pat. No. 1,117,598) are generally used. This process has the drawback that the said basic auxiliaries have to be used in stoichiometric amounts which is not economical and leads, furthermore, to the formation of great amounts of organic and inorganic salts thus raising big problems as to waste water.

It is, furthermore, known, that phenol reacts with phosgene at elevated temperature and under pressure in the presence of catalytic amounts of tertiary amines or N,N-dialkylated acid amides. (cf. U.S. Pat. Nos. 3,211,776 and 3,211,774). This process has the marked drawback that the course of the reaction is not quantitative and therefore, with relatively low yields, the separation of the chloroformic acid phenyl ester from the unreacted phenol becomes very difficult.

It has now been found, that these drawbacks can be avoided when the reaction of phenol, substituted phenols, unsubstituted and substituted naphthols and of compounds containing in the vicinity a second hydroxy group (in the preparation of cyclic carbonates), is effected with phosgene by adding catalytic amounts of a N,N-dialkylated carboxylic acid amide either pressureless or under pressure and care is taken that the hydrogen chloride can escape continuously. Under these conditions, the reaction of the phenols and naphthols with phosgene occurs practically quantitatively and the chloroformic acid aryl esters or carbonates are obtained in high yields and in pure state by simple distillation or recrystallization.

More specifically, it has been found that chloroformic acid aryl esters can be obtained in high yields in a process wherein a liquid phase reaction mixture of a phenol or a naphthol and from 0.5 to about 20 mol percent of an N,N-dialkylacid amide catalyst is formed and phosgene is introduced into that reaction mixture while maintaining the reaction temperature in the range of from 30 — preferably of from 40° to 180° C and the reaction pressure in the range of from atmospheric to about six atmospheres. A stoichiometric deficiency of phosgene with respect to the phenol or naphthol used is maintained in the liquid phase reaction mixture by continuously venting gases, including unreacted phosgene and hydrogen chloride by-product, from the reaction zone during the course of the reaction. After the reaction has been completed under the aforedescribed conditions, the liquid phase is removed from the reaction zone and the chloroformic acid aryl esters are recovered in high yields.

Substituted phenols or substituted naphthols are herein meant to be, above all, compounds which contain one or more substituents being identical or different which are chosen among the following groups:

halogen, such as fluorine, chlorine, bromine, nitro, alkyl having from 1 to 18, preferably from 1 to 6 carbon atoms, phenyl optionally substituted, alkoxy having from 1 to 5 carbon atoms, phenoxy optionally substituted, aralkyl optionally substituted and containing alkylene groups which have from 1 to 8 carbon atoms.

Especially important starting materials, besides the phenol, are compounds which correspond to the general formula

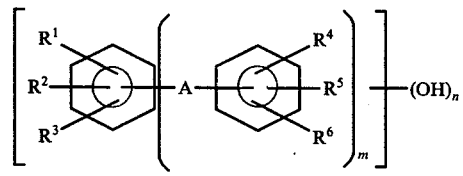

wherein $R^1$, $R^2$, $R^4$ and $R^5$ are identical or different and each represent hydrogen atoms, alkyl groups having from 1 – 12, preferably from 1 – 10, most preferably from 1 – 6 carbon atoms, especially chlorine or bromine atoms, or wherein $R^1$ and $R^2$ and/or $R^4$ and $R^5$ together stand for a condensed benzene radical, $R^3$ and $R^6$ which may be identical or different, each represent chlorine atoms, nitro groups or, preferably, hydrogen atoms, A represents a direct linkage, an oxygen atom or a low alkylene or cycloalkylene group having up to 6 carbon atoms, preferably an alkylene group having from 1 – 3 carbon atoms, $n$ is an integer from 1 to 3, perferably 1 to 2 and $m$ is zero, 1 or 2, preferably zero or 1.

If $n$ is different from 1, the hydroxy groups can be linked to the same or to different aromatic nuclei. All hydroxy groups are converted, according to the process of invention, into chloroformic acid ester groups if they do not stand in ortho- or peri-position one to another, such as, for example, in the pyrocatechin or in 2,3- or 1,8-dihydroxynaphthalene. In this case, the chloroformiates are transformed into the cyclic carbonates by intramolecular reaction.

Compounds in which hydroxy groups are linked to more than one aromatic nucleus are, for example: 4,4'-dihydroxy-diphenyl, 4,4'-dihydroxy-diphenyl-methane, 2,2'-dihydroxy-3,3'-dicyclohexyl -5,5'-dimethyl-diphenylmethane, 2,2-(4',4"-dihydroxy-diphenyl)-propane, 2,2-(3',3"-dimethyl-4',4"-dihydroxydiphenyl)-propane, 2,2-(3',3"-diisopropyl-4',4"-dihydroxydiphenyl)-propane, 2,2-(3',3"-di-tertiary-butyl-4',4"-dihydroxydiphenyl)-propane, 2,2-(4',4"-dihydroxy-diphenyl)-butane or 1,1-(4',4"-dihydroxy-diphenyl)-cyclohexane.

Suitable catalysts are carboxylic acid amines disubstituted at the nitrogen atom of the general formula

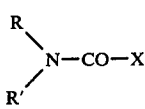

wherein R and R' each represent low alkyl radicals having up to 4, preferably 1 or 2 carbon atoms which may also form, together, an alkylene group having from 4 to 6 carbon atoms, preferably 5, and X represents a hydrogen atom, a low alkyl radical, preferably a methyl radical, or a low molecular dialkylamino group the alkyl radicals of which may be identical or different, preferably contain 1 to 2 carbon atoms, the radicals R or R' each being able to stand together with X for an alkyl group having from 3 to 5 carbon atoms, preferably for a 1,3-propylene group.

Especially suitable catalysts for the process of the invention are, for example, N,N-dimethyl-formamide, N,N-diethylformamide, N,N-dimethyl-acetamide, N,N,N',N'-tetramethyl-urea, N-methyl-pyrrolidone and N-acetyl-piperidine.

Instead of the catalysts mentioned above, the reaction products thereof obtained with phosgene or chloroformic acid phenyl ester of the general formula

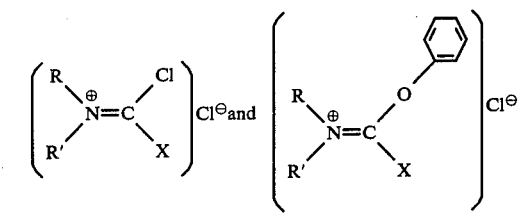

respectively, wherein R, R' and X each are defined as above, may also be used.

To obtain high yields, the catalysts mentioned above are used only in slight amounts in the process of the invention, generally in an amount of from 0.5 to 5 mole %. The slighter the amount of catalyst used, the higher the yield of phenyl ester. To increase the reaction speeds, however, greater amounts of catalyst may be used, for example, within the range of from about 10 to about 20 mole %. When proceeding in this manner, however, smaller yields of chloroformic acid phenyl ester are obtained at first, but given the fact that the residue which remains after its isolation by distillation virtually consists in the reaction product of chloroformic acid ester and the acid amide used, it may be further employed as catalyst and supplies high yields at high reaction speed.

The temperatures at which the reaction may be carried out are within the range of from 40° to 180° C. Phosgenation, however, is more preferably effected at from 70° to 130° C as in this temperature range at high reaction speeds there is hardly any formation of by-products, above all diphenyl carbonate. When working, however, in an inert solvent, for example, chlorobenzene, or if the solidification point of the reaction mixture is below the melting point of the phenol, for example, by previous formation of chloroformic acid ester, the reaction may, in this case, already be carried out at a temperature of about 30° C.

The pressures at which the reaction may be carried out are broadly within the range of about atmospheric pressure to about six atmospheres. Preferably, phosgenation is effected at a pressure of from about atmospheric to about two atmospheres.

Products the melting point of which is above the reaction temperature are advantageously worked in solution or in suspension, suitable solvents being those which are inert to phosgene, such as, for example, toluene, xylene, chlorobenzene or butyl acetate.

In all cases after the reaction has been completed, practically no starting product can be detected any more, for example, by gas chromatography.

The reaction is advantageously carried out in such a manner that phosgene is continuously passed through the reaction mixture the excess being formed in each case escaping together with the hydrogen chloride. The phosgene escaping from the reaction mixture can easily be condensed and introduced again into the reaction mixture, while the hydrogen chloride which boils at lower temperature escapes.

By carrying out the reaction as described and continuously venting gases from the reaction zone including unreacted phosgene and by-product hydrogen chloride, a stoichiometric deficiency of phosgene with respect to the phenol used is maintained in the liquid phase reaction mixture until approximately the end of the reaction when substantially all of the phenol has been converted. This means that the molar ratio of phosgene to the phenol in the liquid phase of the reaction zone is below the stoichiometrical molar ratio during most of the reaction. The ratio increases during the course of the reaction as the conversion of the phenol is increased. Preferably, the range of mols phosgene to mols phenol in the liquid phase reaction mixture in the reaction zone is in the range of from 0.01 to 0.95 until 80% of the phenol has been converted.

After elimination of remaining phosgene by blowing with nitrogen and, if desired, of the solvent used by distillation, the chloroformic acid aryl esters or cyclic carbonates are obtained mostly in a yield above 90%. The degree of purity of the chloroformic acid esters can be determined by volumetric analysis evaluating the diisobutyl-amine value in consideration of the increased consumption for the hydrogen chloride set free. The compounds boiling at lower temperatures prepared in accordance with the invention may, if necessary, be purified by distillation, but they may also be further worked in crude state as starting materials in a following reaction as mentioned as follows:

The chloroformic acid aryl esters are valuable intermediates for carbamic acid aryl esters (pharmaceutics, pesticides) and for carbonates and polycarbonates (plastics) as well known in the prior art, for example, in German Patent Specification No. 709,941 (pharmaceuticals), in German Patent Specification Nos. 1,159,929, 1,097,750 and 1,038,277 (herbicides) and in German Patent Specification No. 1,045,657 and in British patent specification No. 808,485 (plastics). The cyclic carbonates are starting products for the preparation of carbamic acid hydroxy-aryl esters and hydroxyaryl-carbonates according to a process as known in "Liebigs Annalen der Chemie" 300 (1898), page 141.

The process of the invention has the advantage over other, known processes for the preparation of chloroformic acid aryl esters and cyclic carbonates, that the reactions are effected almost quantitatively or in very high yields; in addition thereto, the problems as to waste water which have been mentioned above are completely avoided.

The following Examples illustrate the invention.

EXAMPLE 1

In a round flask provided with stirrer, thermometer, introduction tube for phosgene and cooler operating at from −30° to −40° C, a mixture of 94 g of phenol and 3.6 g of N,N-dimethylformamide was heated at 100° C and phosgene was introduced for 5 hours at a speed of 30 g per hour. After the reaction was so completed, the deep-freezing cooler was replaced by a cooler operating with water in order to allow the excess phosgene to excape. The chloroformic acid phenyl ester was distilled in vacuo, at about 85° C under a pressure of 20mm mercury. 142 g (=91% of the theoretical amount) of a product of more than 99.7% were obtained.

EXAMPLE 2

In the device described in Example 1, 94 g of phenol and 1.8 g of N,N-dimethyl-formamide were reacted together at 120° C with 30 g of phosgene per hour. After a reaction time of 6 hours, and subsequent distillation, 147 g (=94% of the theoretical amount) of a 99.9% chloroformic acid phenyl ester were obtained.

EXAMPLE 3

In a reaction vessel provided with stirrer, thermometer and introduction tube for phosgene, a mixture of 94 g of phenol and 4.4 g of N,N,N',N'-tetramethyl urea were heated at 120° C and phosgene was led through at a speed of 100 g per hour. The introduction of phosgene was interrupted after 5 hours and the reaction mixture was distilled. 144 g (=92% of the theoretical amount) of a 99% chloroformic acid phenyl ester were obtained.

EXAMPLE 4

The reaction was carried out as described in Example 3. The reaction vessel used in this case, was, however, a pressure vessel provided with a relief valve which allowed the hydrogen chloride and the excess phosgene to escape only to such a degree that in the reaction vessel a pressure of 1 atmosphere gauge was maintained. After phosgenation had been completed, the pressure was released and the chloroformic acid phenyl ester was separated from the reaction mixture by distillation. The yield and purity corresponded to that of the product obtained according to the process described in Example 3.

EXAMPLE 5

(a) In a device provided with a deep-freezing cooler as described in Example 1 a mixture of 94 g of phenol and 15 g of N,N-dimethyl-formamide was reacted at 80° C within 3 hours with 150 g of phosgene. After the reaction had been completed, the mixture was distilled. About 110g of chloroformic acid phenyl ester were obtained. In the distillation flask, a strongly hygroscopic residue remained wich served as catalyst for the following reaction.

(b) The distillation residue which remained after the reaction as described in Example 5a was mixed with 95 g of phenol and reacted with phosgene in the same manner as described in Example 5a. After working up 149 g (=95.0% in theory) of chloroformic acid ester were obtained. The distillation residue could again be used as phosgenation catalyst.

EXAMPLE 6

1.8 g of N,N-dimethyl-formamide were dissolved in 50 ml of benzene and about 5 g of phosgene were introduced at room temperature. The dimethyl-formamide chloride formed a colorless precipitate. Now, the benzene was separated by distillation in vacuo up to a sump temperature of 50° C and instead of N,N-dimethyl-formamide the remaining residue was used as catalyst for the reaction of phenol with phosgene in an analogous manner as described in Example 2. The phenyl ester was obtained in about the same yield and purity as the product described in Example 2.

EXAMPLE 7

1.8 g of N,N-dimethyl-formamide were dissolved in 50 ml of benzene, 3.9 g of chloroformic acid phenyl ester were added and the mixture was heated at 50° C while stirring. This caused the formation of gas and a slightly yellow precipitate was separated. After the gas formation had finished, the solvent was separated by distillation in vacuo up to a sump temperature of 50° C and instead of dimethyl formamide the remaining residue was used in the same way as described in Example 2. The yield and purity of the chloroformic acid phenyl ester corresponded to that described in Example 2.

EXAMPLES 8 – 12

In the same manner as indicated in the testing prescription described in Example 3, 94 g of phenol were reacted with phosgene by the addition of the acid amides enumerated in the Table established hereinafter. After having worked up by distillation, the chloroformic acid phenyl ester was obtained in the yield indicated in the Table having a degree of purity constantly above 99%.

TABLE

| Example No. | Acid Amide | Yield % in theory |
|---|---|---|
| 8 | 3.6 g of N,N-dimethyl-formamide | 91.0 |
| 9 | 5.0 g of N,N-diethyl-formamide | 90.5 |
| 10 | 4.3 g of N,N-dimethyl-acetamide | 88.5 |
| 11 | 4.9 g of N-methyl-purrolidone | 90.5 |
| 12 | 6.3 g of N-acetyl-piperidine | 89.5 |

EXAMPLE 13

In a round flask provided with stirrer, thermometer, an introduction tube for phosgene and a reflux cooler operating at about −30° C a mixture of 150 g of o-sec.-butylphenol and 4 g of N,N,N',N',-tetramethyl urea was heated at 100° C and phosgene was introduced to such a degree that the phosgene reflux in the deep-freezing cooler did not increase so much as to reduce the sump temperature. After a reaction time of about 5 hours and a phosgene consumption of about 190 g the reflux cooler was replaced by a descending cooler so that the greatest part of the excess phosgene could be separated from the reaction mixture by distillation. The rest of phosgene was blown out with dry nitrogen. Thus, a yield of about 97% of chloroformic acid-o-sec.-butyl-phenyl-ester was obtained which was practically free from the starting product (GC).

EXAMPLES 14 – 31

In an analogous manner as described in Example 13, the phenols and naphthols indicated in the following Table can be reacted with phosgene to yield the corresponding chloroformic acid esters. According to this method, the solid products at the corresponding reaction temperature were reacted in the solvent as indicated.

| Ex. No. | Starting Product | Catalyst | Solvent | Temperature °C | Time in hours | Yield in of theory | Boiling point °C/mm mercury |
|---|---|---|---|---|---|---|---|
| 14 | 150 g o-sec. butylphenol | 2,5 g DMF | — | 100 | 7.5 | 94.0 | 71/1 |
| 15 | 150 g p-sec. butylphenol | 5,5 g TMU | — | 100 | 2 | 94.8 | 80/1 |
| 16 | 68 g m-isopropylphenol | 1.0 g TMU | — | 100 | 8.5 | 94.0 | 68/1 |
| 17 | 128,5 g o-chlorophenol | 4.0 g TMU | — | 120 | 6.5 | 86.7 | 55/1 |
| 18 | 64,25 g p-chlorophenol | 1.0 g TMU | — | 100 | 7.5 | 94.5 | 60/1 |
| 19 | 81,5 g 2,4-dichlorophenol | 1.0 g TMU | — | 80 | 9.5 | 94.3 | 75/1 |
| 20 | 49,4 g 2,4,5-trichlorophenol | 2.0 g TMU | 5 g chlorobenzene | 85 | 4 | 95.8 | 94/1 |
| 21 | 124 g p-methoxyphenol | 2.3 g TMU | — | 100 | 3.5 | 98.0 | 77/1 |
| 22 | 110 g p-nonylphenol | 2.0 g TMU | — | 100 | 3 | 93.2 | 115/0.5 |
| 23 | 69,5 g o-nitrophenol | 2.0 g TMU | — | 80 | 3.5 | 89.3 | |
| 24 | 65,8 g p-nitrophenol | 1.0 g TMU | 65.8 g chlorobenzene | 85 | 3.5 | 90.7 | |
| 25 | 144 g α-naphthol | 5.5 g TMU | 10 — | 100 | 3 | 94.0 | 105/1 |
| 25a | 144 g α-naphthol | 5.5 g TMU | 144 g xylene | 80 | 6 | 95.0 | 105/1 |
| 25b | 144 g α-naphthol | 5.0 g TMU | 144 g butyl-acetate | 80 | 9 | 87.8 | 105/1 |
| 26 | 89,25 g 4-chloro-α-naphthol | 1.0 g TMU | 89.25 g chlorobenzene | 100 | 4.5 | 87.1 | 126/1 |
| 27 | 144 g β-naphthol | 2.0 g TMU | 144 g chlorobenzene | 100 | 4.5 | 98.2 | 112/1 |
| 28 | 89.25 g 1-chloro-β-naphthol | 1.0 g TMU | — | 120 | 4.5 | 91.4 | 129/1 |
| 29 | 110 g hydroquinone | 7.0 g TMU | 110 g chlorobenzene | 90 | 7 | 91.5 | 116/3 |
| 30 | 114 g 2,2-(4', 4''-dihydroxy-diphenyl)-propane | 2.3 g TMU | 450 g chlorobenzene | 115 | 8.5 | 94 | >200/0.5 |
| 31 | 71,25 g 2-methyl-4-chloro-phenol | 2.0 g TMU | — | 100 | 2.0 | 95.2 | 68/1 |

DMF = N,N-dimethylformamide
TMU = N,N,N',N'-tetramethyl urea

EXAMPLE 32

A mixture of 55 g of pyrocatechin, 55 g of chlorobenzene and 2 g of tetramethyl urea were heated at 100° C. At that temperature, phosgene was introduced to such a degree that there was only slight reflux in a reflux cooler operating with a cooling liquid of −20° C. After about 4 hours, the reaction was completed. About 110g of phosgene were consumed and the phosgene reflux in the deep-frozen reflux cooler was increased. Then, the greatest part of the excess phosgene was degased by eliminating the cooling liquid, the phosgene being collected via a descending distillation cooler operating with a deep-frozen liquid. Then, the residue was distilled off together with the solvent.

The yield obtained was about 97% of pyrocatechin carbonate having the formula

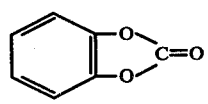

which was distilled in vacuo to be further purified.
Boiling point: 151° C/120 mm mercury;
Solidification point: 119° C;
Yield: 63 g (93% in theory).

EXAMPLE 33

A mixture of 40 g of 2,3-dihydroxy-naphthalene, 40 g of chlorobenzene and 1 g of tetramethyl urea was treated with phosgene at 120° C for 2 hours in the same manner as described in Example 32. After having eliminated the excess phosgene by degasing, the mixture was filtered in hot state; the 2,3-dihydroxy-naphthalene-carbonate in the filtrate was crystallized out by adding petroleum ether or gasoline and cooling the solution to 5° C. After suction-filtration and washing with petroleum ether or gasoline 42 g (=90.5% in theory) of the cyclic carbonate having a solidification point of 158° C were obtained. Condensation of the mother liquor yielded further amounts of the product.

Analysis: Calculated: C 71.0%: H 3.2%: O 25.8%.
Found: C 70.9%: H 3.2%: O 25.6%. C 70.7%: H 3.4%: O 25.8%.

The structure was also confirmed by mass spectrography.

EXAMPLE 34

1,8-Dihydroxy-naphthalene was treated with phosgene in an analogous manner as described in Example 33. After a 3.5 hours phosgenation and following working up 1,8-dihydroxy-naphthalene-carbonate was obtained in a yield of about 90% and had a melting point of 135° C.

Analysis: Calculated: C 71.0%: H 3.2%: O 25.8%.
Found: C 71.2%: H 3.4%: O 25.2%. C 71.5%: H 3.4%: O 25.2%.

The structure was also confirmed by mass spectrography.

EXAMPLE 35

A mixture of 62 g of 4-methyl-pyrocatechin, 62 g of xylene and 1 g of tetramethyl urea was treated with phosgene at 120° C for 3 hours in an analogous manner as described in Example 32. Then, the reaction mixture was freed from the excess phosgene by heating at reflux temperature and the solvent was distilled in vacuo. 4-methyl-pyrocatechin-carbonate was obtained in a yield of about 97% which was distilled in vacuo for further purification. Yield: 71.3 g (=95.1% in theory); Boiling point: 89° C/3 mm mercury; solidification point 33.5°–34° C.

What is claimed is:

1. A process for preparation of chloroformic acid aryl esters in high yields comprising the steps of: forming a liquid phase reaction mixture in a reaction zone, said reaction mixture comprising a phenol or naphthol and from 0.5 to about 20 mol percent of said phenol or naphthol of an N,N-dialkyl acid amide; introducing phosgene into said liquid phase reaction mixture in said reaction zone and reacting said phosgene and said phenol or naphthol at a temperature of 30° to 180° C and at a pressure of from atmospheric pressure to six atmospheres; continuously venting gases from said reaction zone during the course of said reaction, said vented gases including unreacted phosgene and by-product hydrogen chloride, and thereby maintaining a molar ratio of phosgene to phenol or naphthol, in said liquid phase reaction mixture, in the range of from 0.01 to 0.95, until 80% of said phenol or naphthol has been converted; and thereafter removing the liquid phase reaction mixture from the said reaction zone and recovering the chloroformic acid aryl esters therein.

2. A process as claimed in claim 1, wherein substituted phenols or substituted naphthols are reacted which contain as substituents halogen atoms, nitro groups, alkyl groups having from 1 to 18 carbon atoms, substituted phenyl radicals, alkoxy groups having from 1 to 5 carbon atoms, substituted phenoxy groups or substituted aralkyl radicals having alkylene groups of from 1 to 6 carbon atoms.

3. A process as claimed in claim 1, wherein the phenols and naphthols are of the formula

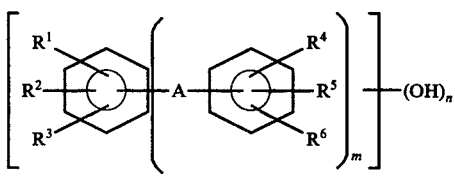

wherein $R^1$, $R^2$, $R^4$ and $R^5$ each is identical or different and represents hydrogen atoms, alkyl groups having from 1 to 12 carbon atoms, alkoxy groups having from 1 to 4 carbon atoms or halogen atoms or $R^1$ and $R^2$ and/or $R^4$ and $R^5$ together represent a condensed benzene radical, $R^3$ and $R^6$ which may be identical or different, each represents hydrogen atoms or chlorine atoms or nitro groups, A is a direct linkage, an oxygen atom or a lower alkylene or cycloalkylene group having up to 6 carbon atoms, $n$ is a whole number from 1 to 3 and $m$ is zero or 1 or 2.

4. A process as claimed in claim 1, wherein the phenolic compounds are of the formula

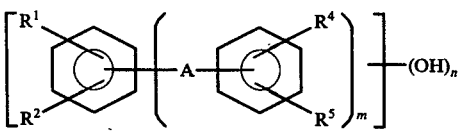

wherein $R^1$, $R^2$, $R^4$ and $R^5$ are identical or different and each represents a hydrogen, a chlorine or a bromine atom, alkyl groups having from 1 to 6 carbon atoms, alkoxy groups having from 1 to 4 carbon atoms or $R^1$ and $R^2$ together represent a condensed benzene radical, A is a direct linkage, an oxygen atom or an alkylene group having from 1 to 3 carbon atoms, $n$ is 1 or 2 and $m$ is zero or 1.

5. A process a claimed in claim 1, wherein the reaction is effected under atmospheric pressure.

6. A process as claimed in claim 1, wherein carboxylic acid amides disubstituted at the nitrogen atoms of the formula

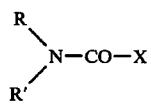

are used wherein R and R' each represents a lower alkyl radical or together an alkylene radical having from 4 to 6 carbon atoms and X represents a hydrogen atom, a lower alkyl radical or a low-molecular dialkyl-amino group and R and R' and X together may represent an alkylene group having from 3 to 5 carbon atoms.

7. A process as claimed in claim 1, wherein N,N-dimethyl-formamide or N,N,N',N'-tetramethyl urea is used.

8. A process as claimed in claim 1, wherein the reaction product of N,N-dialkylated carboxylic acid amide with phosgene or with chloroformic acid phenyl ester of the formula

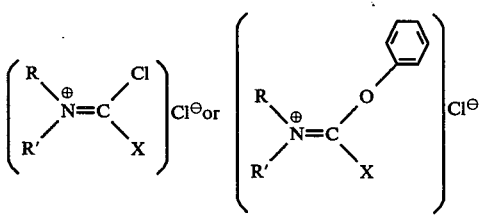

are used wherein R, R' and X are defined as above.

9. A process as claimed in claim 1, wherein the reaction is carried out at a temperature of from 40° to 180° C.

10. A process as claimed in claim 1, wherein the reaction is carried out at a temperature of from 40° to 130° C.

11. A process as claimed in claim 1, wherein the reaction is carried out at a temperature of from 70° to 130° C.

* * * * *